(12) United States Patent
Itoh et al.

(10) Patent No.: US 7,331,232 B2
(45) Date of Patent: Feb. 19, 2008

(54) MEASUREMENT METHOD AND BIOSENSOR APPARATUS USING RESONATOR

(75) Inventors: Atsushi Itoh, Kanagawa (JP); Motoko Ichihashi, Kanagawa (JP)

(73) Assignee: ULVAC, Inc., Chigasaki (JP)

( * ) Notice: Subject to any disclaimer, the term of this patent is extended or adjusted under 35 U.S.C. 154(b) by 202 days.

(21) Appl. No.: 10/947,326

(22) Filed: Sep. 23, 2004

(65) Prior Publication Data

US 2005/0069864 A1 Mar. 31, 2005

(30) Foreign Application Priority Data

Sep. 25, 2003 (JP) ............................. 2003-333623
Jun. 29, 2004 (JP) ............................. 2004-192154

(51) Int. Cl.
*G01N 29/00* (2006.01)
*G01G 3/16* (2006.01)

(52) U.S. Cl. ...................... 73/590; 73/61.49; 73/61.79; 73/64.53

(58) Field of Classification Search ............... 73/54.41, 73/61.49, 61.79, 64.53, 590
See application file for complete search history.

(56) References Cited

U.S. PATENT DOCUMENTS 4,741,200 A * 5/1988 Hammerle ................. 73/54.25
5,201,215 A * 4/1993 Granstaff et al. .......... 73/54.41

FOREIGN PATENT DOCUMENTS

JP 2001-304945 10/2001

OTHER PUBLICATIONS

European Search Report dated Dec. 29, 2004.

* cited by examiner

*Primary Examiner*—Daniel S. Larkin
(74) *Attorney, Agent, or Firm*—Kratz, Quintos & Hanson, LLP

(57) ABSTRACT

A measurement method and a biosensor apparatus using a resonator with which it is not necessary to agitate a sample solution in a cell and even if the amount of the sample solution is very small the influence of pressure waves is greatly reduced and extremely easy and accurate measurement is possible. In a method of the kind wherein a sample solution is brought into contact with one side of a resonator having first and second electrodes on opposite sides of a crystal plate and an a.c. signal is applied across the first and second electrodes and a frequency change of the resonator is measured from a relationship between the frequency of the a.c. signal and an electrical characteristic of the resonator, the resonator is made to oscillate at an N-tuple harmonic (N=3, 5, 7 . . . ) as the frequency change is measured.

10 Claims, 9 Drawing Sheets

IN AIR

IN LIQUID

MEASUREMENT METHOD AND BIOSENSOR APPARATUS USING RESONATOR

BACKGROUND OF THE INVENTION

This invention relates to a measurement method and a biosensor apparatus using a resonator, used for example for the tracking and state analysis of chemical reactions in the fields of biochemistry, medicine and food.

In a biosensor apparatus using a QCM in related art, as shown in FIG. 17, a sample solution 8 is brought into contact with a piezoelectric device such as a quartz resonator 7 mounted at the bottom of a cylindrical cell 15, and either the quartz resonator, which is a sensor, is oscillated at its fundamental harmonic resonant frequency and a frequency change is measured, or an impedance analyzer is used to measure the frequency of the fundamental harmonic resonance point (the point at which the impedance is at a minimum) continuously, and from this frequency change the quantity of a material adsorbed to the piezoelectric device surface is measured.

However, during this measurement, frequency fluctuations over a range of several hundred Hz with a substantially constant period have arisen.

The reason for this is thought to be that pressure waves caused by the displacement of the quartz resonator are reflected at the liquid surface, and when with a load acting on the quartz resonator a change in the shape of the liquid surface caused by vibration of the liquid surface occurs or a fall of the liquid surface caused by evaporation of the solution occurs, the load fluctuates (Martin, B. A.; Hager, H. E.: J. Appl. Phys. 1989, "Flow profile above a quartz crystal vibrating in liquid").

Because of this, in measurement methods of related art using the fundamental harmonic of the resonator, it has been necessary to reduce pressure waves by disturbing the liquid surface by moving up and down and/or rotating a stirring rod inside the cell or by treating the cell so as to make the liquid surface concave. Also, when the amount of the sample solution is very small, because agitating it is impossible and furthermore the liquid surface becomes convex due to surface tension, it has been impossible to avoid the influence of the above-mentioned frequency fluctuation.

SUMMARY OF THE INVENTION

It is therefore an object of the present invention to provide a measurement method and a biosensor apparatus using a resonator with which it is not necessary to agitate the sample solution in the cell and even if the amount of the sample solution is very small the influence of pressure waves is greatly reduced and extremely easy and accurate measurement is possible.

As a result of assiduous research aimed at achieving this object and other objects, the present inventors discovered that it is possible to reduce the influence of the above-mentioned pressure waves by not measuring frequency change using the resonant frequency at the fundamental harmonic of the resonator but rather measuring frequency change of a resonant frequency at an N-tuple harmonic (N=3, 5, 7 . . . ) or in the vicinity of an N-tuple harmonic resonant frequency.

The theory behind it being possible to reduce the influence of pressure waves like this is as follows. The equivalent circuit of a piezoelectric device such as a quartz resonator in atmospheric air is as shown in FIG. 14A, but when one side of it is immersed in water the equivalent circuit parameters become as shown in FIG. 14B.

At this time, according to the literature (Thomas W. Schneider and Stephen J. Martin: Anal. Chem. 1995, 67, 3324-3335), the motional resistance (resistance due to vibration) R2 is as given by the following Exp. 1.

$$R2 = N\pi/4K^2 \omega_s C_0 Z_q \times [(\omega\rho\eta/2)^{1/2} + P(\kappa\rho)^{1/2}] \qquad \text{Exp. 1}$$

$$P = (\lambda/2\pi)^2 \qquad \text{Exp. 2}$$

Exp. 2 expresses the gradient of the displacement of the oscillation.

With R2 in Exp. 1, the resonant frequency Fs of a quartz resonator varies greatly.

This R2 component can be divided into the following two components, called a shear wave (Exp. 3) and a compression wave (Exp. 4).

$$R2_{shear} = N\pi/4K^2 \omega_s C_0 Z_q \times (\omega\rho\eta/2)^{1/2} \qquad \text{Exp. 3}$$

$$R2_{comp} = N\pi/4K^2 \omega_s C_0 Z_q \times P(\kappa\rho)^{1/2} \qquad \text{Exp. 4}$$

$R2_{shear}$ depends on the viscous load on the liquid resulting from the shear wave, and this shear wave is attenuated when it enters the liquid from the quartz resonator surface, as shown in FIG. 15. The distance σ to the point at which the shear wave is attenuated is given by the following Exp. 5, and in the case of a 5 MHz quartz resonator is about 0.25 μm.

Accordingly, since this shear wave cannot reach the liquid surface, $R2_{shear}$ always shows a fixed value.

$$\sigma = (2\eta/\omega\rho)^{1/2} \qquad \text{Exp. 5}$$

In the case of $R2_{comp}$, on the other hand, from the gradient created by the oscillation displacement a pressure wave arises in the liquid, as shown in FIG. 16, and this reaches the liquid surface and results in a pressure wave between the liquid surface and the quartz resonator.

Consequently, when the height of the liquid surface changes, this value changes over a range of 0 to $R2_{comp\ max}$. This $R2_{comp}$ reaches a maximum when the height of the liquid surface is h=nλ/2 (N=1, 2, 3 . . . ), and is 0 when h=(n+1)λ/2 (N=1, 2, 3 . . . ).

For example, when one side of a quartz resonator of diameter 8.9 mm and of, 9 MHz is immersed in pure water, a periodic waviness of about 48 Hz arises in Fs. At this time, R1=100 Ω, $R2_{shear}$=353 Ω and $R2_{comp}$=13 Ω, and the frequency change due to viscous load occurring when one side of a 9 MHz quartz resonator is immersed in pure water from being in atmospheric air is 1330 Hz.

Therefore, the relationship between this wavy Fs and $R2_{comp}$ is as shown by the following Exp. 6, and the periodic displacement of Fs and the frequency change due to $R2_{comp}$ match.

$$R2_{comp}/R2_{shear} \times \Delta F_s \text{ of viscous load} = 13/353 \times 1330 = 49 \text{ Hz} \qquad \text{Exp. 6}$$

Also, from Exp. 2, Exp. 3 and Exp. 4, at the N-tuple harmonic $R2_{shear}$ is the ½ power of N times the fundamental harmonic and $R2_{comp}$ is the second power of 1/N times the fundamental harmonic.

Therefore, the frequency displacement due to the influence of $R2_{comp}$ at the N-tuple harmonic is the 5/2 power of 1/N times the fundamental harmonic.

In this invention, on the basis of this theory, the following means for solving the problems described above were found out.

That is, in a first aspect, the invention provides a measurement method of the kind wherein a sample solution is brought into contact with one side of a resonator having first and second electrodes on opposite sides of a crystal plate and an a.c. signal is applied across the first and second electrodes and a frequency change of the resonator is measured from a relationship between the frequency of the a.c. signal and an electrical characteristic of the resonator, wherein the resonator is made to oscillate at an N-tuple harmonic (N=3, 5, 7 . . . ) as the frequency change is measured.

In a second aspect of the invention, in the method of the first aspect, the sample solution is brought into contact only with the surface of an electrode.

In a third aspect, the invention provides a biosensor apparatus of the kind wherein a sample solution is brought into contact with one side of a resonator having first and second electrodes on opposite sides of a crystal plate and an a.c. signal is applied across the first and second electrodes and a frequency change of the resonator is measured from a relationship between the frequency of the a.c. signal and an electrical characteristic of the resonator, wherein the resonator is made to oscillate at an N-tuple harmonic (N=3, 5, 7 . . . ) as the frequency change is measured.

In a fourth aspect of the invention, the sample solution is brought into contact only with the surface of an electrode.

In a fifth aspect of the invention, the biosensor in the third aspect or the fourth aspect comprises a cell for holding the sample solution in contact with the resonator, and the amount of sample solution held by the cell is less than 100 μl.

In a sixth aspect of the invention, in the biosensor according to the fourth aspect, when the oscillation frequency of the resonator is made 9 MHz the amount of sample solution brought into contact with the electrode surface is not greater than the amount obtained by multiplying the diameter of the electrode (mm) by the coefficient 12.5 μl/mm.

In a seventh aspect of the invention, in the biosensor according to the fourth aspect, when the oscillation frequency of the resonator is made 27 MHz the amount of sample solution placed on the electrode surface is not greater than the amount obtained by multiplying the diameter of the electrode (mm) by the coefficient 12.0 μl/mm.

In an eighth aspect of the invention, in the biosensor according to the third or fourth aspect, the surface of the crystal plate around the electrode is made water-repellent.

In a ninth aspect of the invention, in the biosensor according to the third or fourth aspect, the resonator is disposed in a humidified atmosphere.

And in a tenth aspect of the invention, in the biosensor according to the third or fourth aspect, multiple resonators are disposed adjacently on the same substrate.

With a measuring method according to the invention, without contriving means for agitating the sample solution in which the electrode is immersed to disturb the liquid surface or making that liquid surface concave, it is possible to reduce pressure waves influencing measured frequencies, and highly accurate measurement becomes possible. And even when a very small droplet of sample solution is dripped onto the electrode so that the liquid surface is convex, because measurement is carried out with the sample solution dripped onto the electrode only, the occurrence of frequency change in a fixed direction (drift) can be suppressed, and when a very small amount of sample solution is measured still more accurate measurement is possible and furthermore it is possible to reduce the amount of a valuable sample solution used.

And with a biosensor apparatus according to the invention, because it is possible to suppress the effects of pressure waves, highly accurate measurement is possible. And even when the amount of sample solution held is less than 100 μl, it is not necessary to stir or otherwise agitate the sample solution. And by making the amount of sample solution below a predetermined amount with respect to the diameter of the electrode, it is possible to suppress the occurrence of frequency change in a fixed direction (drift), and when a very small amount of sample solution is measured still more accurate measurement is possible and furthermore it is possible to reduce the amount of a valuable sample solution used. Also, by making the surface of the crystal plate around the electrode water-repellent it is possible to make it easy to place a very small amount of sample solution on the electrode only.

BRIEF DESCRIPTION OF THE DRAWINGS

Preferred embodiments of the invention will now be described with reference to the drawings, in which.

DETAILED DESCRIPTION OF THE PREFERRED EMBODIMENTS

The resonant frequency at the fundamental harmonic mentioned above refers to the frequency at which resonance occurs when, with the sample solution to be the object of measurement brought into contact with the cell, the resonator is oscillated at its fundamental harmonic.

In this invention, not the resonant frequency at the fundamental harmonic but rather the resonant frequency at an N-tuple harmonic (N=3, 5, 7 . . . ; that is, N=2n+1, where n is an integer not less than 1. Hereinafter written 'N-tuple harmonic'.) is used. Specifically, when the resonant frequency at the fundamental harmonic is 27 MHz, the resonant frequency at the triple harmonic is 81 MHz. Here, the resonant frequency at an N-tuple harmonic includes frequencies near the N-tuple harmonic resonant frequency as well as the N-tuple harmonic resonant frequency, and for example includes up to scanning a range of about ±500 kHz.

In the measurement of frequency change, when an impedance analyzer is used, one is not necessarily limited to measuring the point of minimum impedance. For example, it is also possible to use a half value frequency previously proposed by the present applicants (Japanese Patent Application 2003-120335), which is a half value frequency that induces a half value conductance half the size of the conductance of when the resonator is in series resonance, and is a frequency near to the resonant frequency that induces the series resonance and larger than the resonant frequency. And it is also possible to use at least two frequencies from among a group of three frequencies consisting of the resonant frequency that puts the resonator in series resonance and first and second half value frequencies that induce half value conductances half the size of the conductance of when the resonator is in series resonance, similarly proposed previously (Japanese Patent Application 2003-120370). Therefore, besides pressure wave, there is no influence of viscosity effect when a sample which is different from a buffer solution in viscosity is used and of viscosity effect due to temperature change, so that accurate measurement becomes possible.

A preferred embodiment of the invention will now be described with reference to the accompanying drawings. However, the invention is not limited to this preferred embodiment.

Figure 1:
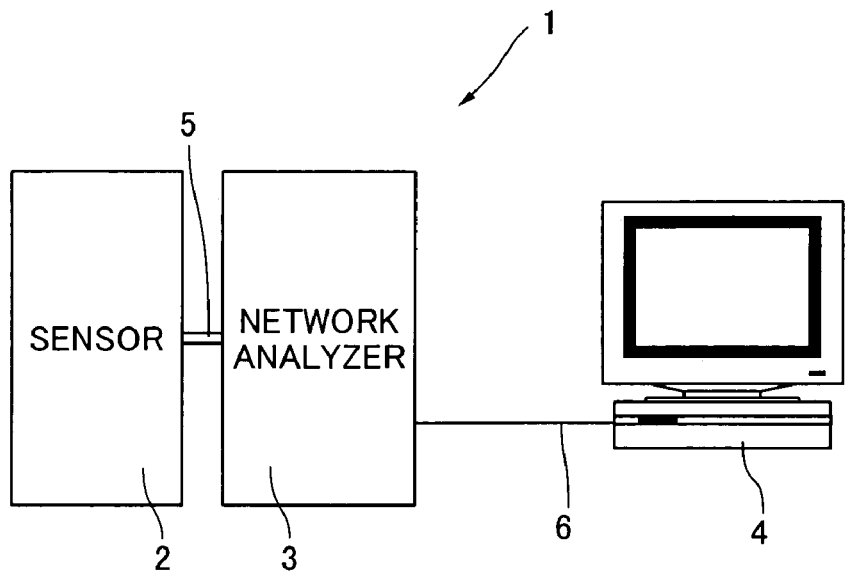
FIG. 1 is a view illustrating a preferred embodiment of a biosensor apparatus according to the invention.

The reference number 1 in FIG. 1 denotes a biosensor apparatus constituting a preferred embodiment of the present invention.

This biosensor apparatus 1 has a sensor part 2, a network analyzer 3 and a computer 4. The sensor part 2 and the network analyzer 3 are connected by a cable 5, and the network analyzer 3 and the computer 4 are connected by a cable 6. The sensor part 2 has a quartz resonator 7.

Figure 2A:
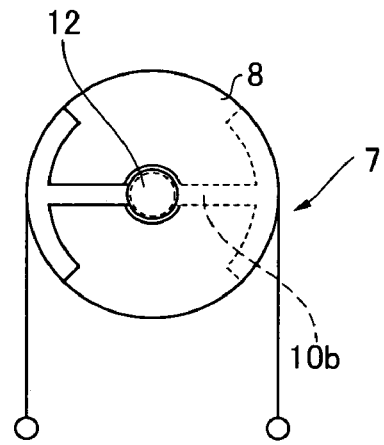
FIG. 2A is a plan view and FIG. 2B a sectional view of a quartz resonator of the biosensor apparatus.
Figure 2B:
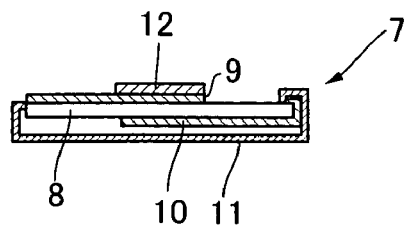

As shown in plan view in FIG. 2A and in sectional view in FIG. 2B, the quartz resonator 7 provided in the sensor part 2 has a first metal electrode 9 and a second metal electrode 10 on a front side and a rear side respectively of a quartz crystal plate 8 formed in the shape of a disc. The metal electrodes 9 and 10 shown in the figures are each formed in the shape of a disc and have lead wires 9b, 10b respectively connected to them. The second metal electrode 10 on the rear side is covered by a resin cover 11, as shown in FIG. 2B, so that when the quartz resonator 7 is put in a liquid solution, the second metal electrode 10 on the rear side is not exposed to the solution, and oscillation is possible. On the other hand, on the surface of the first metal electrode 9 on the front side, a reaction material 12 constituted to react with a specified component and adsorb that component is disposed so that it makes contact with the sample solution during measurement.

Figure 3:
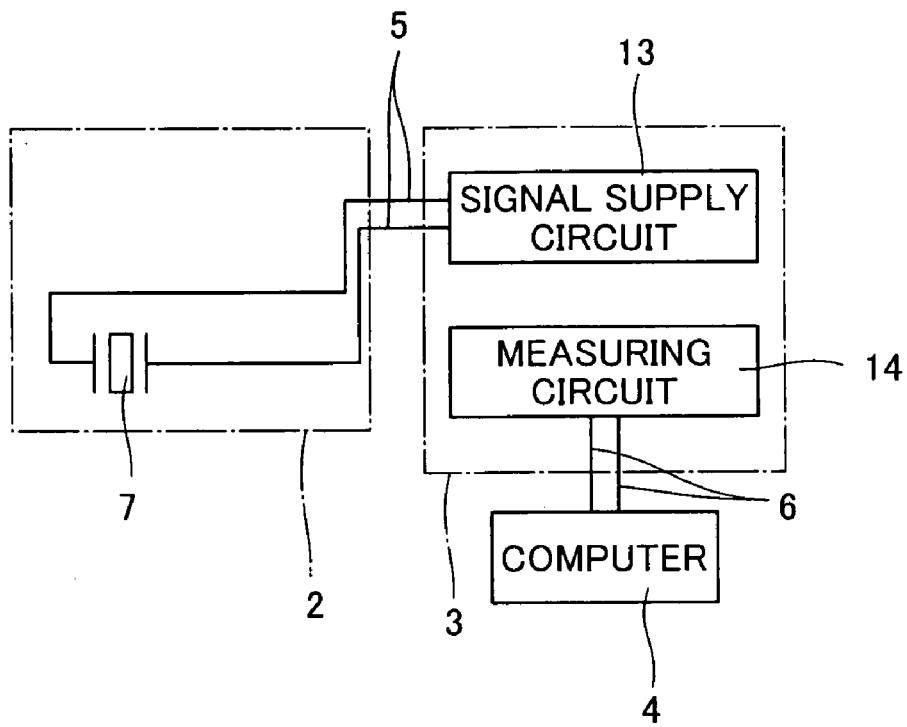
FIG. 3 is a block diagram of the biosensor apparatus.

As shown in FIG. 3, the network analyzer 3 has a signal supply circuit 13 and a measuring circuit 14.

The signal supply circuit 13 is constructed to output an a.c. input signal while changing its frequency.

The measuring circuit 14 is constructed to measure an electrical characteristic such as the resonant frequency or the phase of the quartz resonator 7 on the basis of an output signal from the quartz resonator 7 and the input signal outputted from the signal supply circuit 13, and to output these to the computer 4.

The computer 4 is constructed to obtain a reaction rate of a component in the sample solution and analyze the component on the basis of a measured electrical characteristic such as a frequency characteristic of the quartz resonator 7.

A procedure for using the biosensor apparatus 1 constructed as described above to analyze the state of a reaction between a specified component in a sample solution such as for example blood and the reaction material 12 disposed on the surface of the quartz resonator 7 will now be described.

Figure 17:
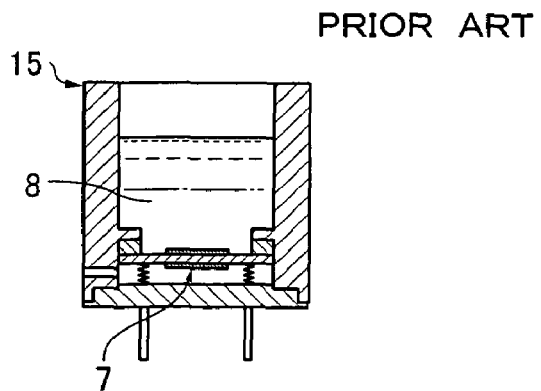
FIG. 17 is a view illustrating a cell of a biosensor apparatus.

First, as shown in FIG. 17, a sample solution 8 is poured into a cylindrical cell 15 having the quartz resonator 7 disposed at its bottom, and with the quartz resonator 7 immersed in the sample solution 8 the network analyzer 3 is started up and a control signal is outputted from the computer 4. On the basis of the outputted control signal, an input signal outputted from the signal supply circuit 13 is outputted to the sensor part 2 via the cable 5.

When the input signal is supplied to the quartz resonator 7 from the signal supply circuit 13, the quartz resonator 7 supplied with the input signal outputs an output signal in correspondence with the input signal. This output signal is outputted via the cable 5 to the network analyzer 3 and is inputted to the measuring circuit 14 in the network analyzer 3. The measuring circuit 14 then detects the signal strength (here, equivalent to the amplitude of the oscillation frequency) of the output signal from the quartz resonator 7 supplied with the input signal.

Figure 4:
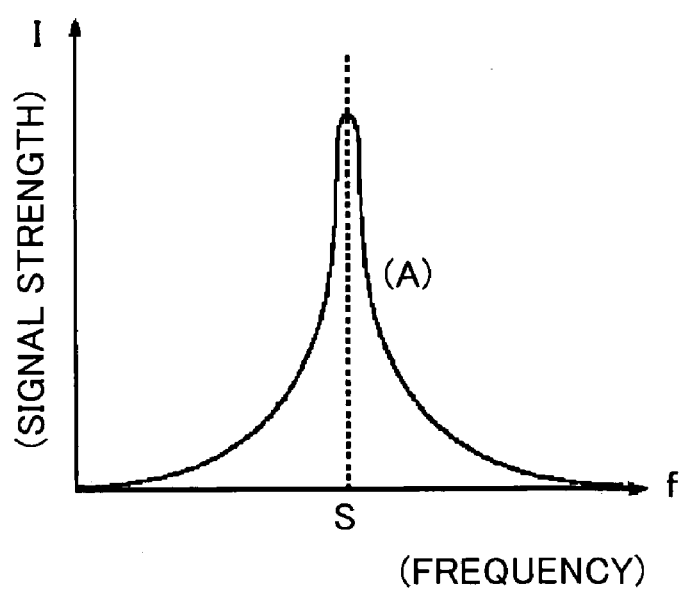
FIG. 4 is a chart showing a relationship between the frequency S of an input signal and a signal strength I.

The signal supply circuit 13 changes the frequency of the input signal within a predetermined frequency range, and the measuring circuit 14 detects the signal strength of the output signal every time the input signal frequency is changed. As a result, a relationship between the frequency of the input signal and the signal strength of the output signal is obtained. Specifically, as in the relationship between the frequency S of an input signal and a signal strength I shown in the curve (A) of FIG. 4, in correspondence with change in the frequency S of the input signal the signal strength I also varies, and at a certain frequency takes a maximum, peak value. At this time, the quartz resonator 7 is resonating, and the frequency in this case is a resonant frequency. The reference symbol S in the figure shows a resonant frequency of the quartz resonator 7.

The measuring circuit 14 measures the resonant frequency of the quartz resonator 7 in this way, and outputs the obtained resonant frequency of the quartz resonator 7 to the computer 4 through the cable 6. Then, after a predetermined time has elapsed, the computer 4 stops the supply of the signal.

In this preferred embodiment, the measurement described above is first carried out at the fundamental harmonic of the quartz resonator 7, and its resonant frequency at the fundamental harmonic is determined. Then, on the basis of the resonant frequency measured, the same measurement as that described above based on the fundamental harmonic is carried out using an N-tuple resonant frequency.

By this measurement, variations of an N-tuple resonant frequency of the quartz resonator 7 constantly inputted from the network analyzer 3 are measured, and using the computer 4 it is possible to measure the reaction state of a component adsorbed to the surface of the reaction material 12, for example by calculating from the N-tuple resonant frequency of the quartz resonator 7 over a predetermined time range a change with time of the mass of the component adsorbed to the surface of the reaction material 12 and obtaining the reaction rate of the reaction material 12 and the component adsorbed thereto on the basis of this change of mass with time.

In this preferred embodiment, as an example of obtaining an electrical characteristic, a resonant frequency is detected; however, the measured frequency does not have to be a resonant frequency, and alternatively for example the phase difference between the phase of the output signal and the phase of the input signal may be measured. In particular, at the point (phase point) where the phase difference is 0°, because the quartz resonator 7 is resonating, the result is the same as in this preferred embodiment of the invention, in which a resonant frequency is obtained.

And, besides the above, a frequency previously proposed by the present applicant (Japanese Patent Application 2003-120335 or Japanese Patent Application 2003-120370) may alternatively be used. When there is an influence of viscosity, more accurate measurement is possible with this approach.

And although as the cell 15 in the foregoing description a cylindrical cell was used in order to use a relatively large amount of sample solution, the use of an N-tuple harmonic of this invention is effective when measuring sample solutions of less than 100 μl, with which stirring or the like is difficult and furthermore the surface of the sample solution tends to be convex.

Figure 13A:
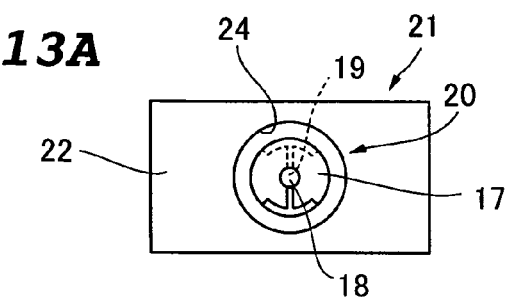
FIG. 13A is a plan view and FIG. 13B a side view illustrating the shape of a cell of Embodiment 5-3.
Figure 13B:
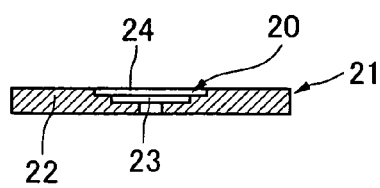
Figure 14A:
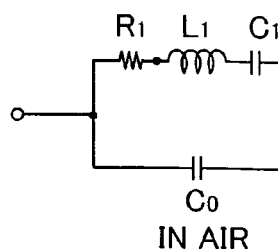
FIGS. 14A and 14B are views illustrating a theory underlying the invention, FIG. 14A being a view showing an equivalent circuit of a quartz resonator in atmospheric air and FIG. 14B a view showing an equivalent circuit of a quartz resonator in a liquid.
Figure 14B:
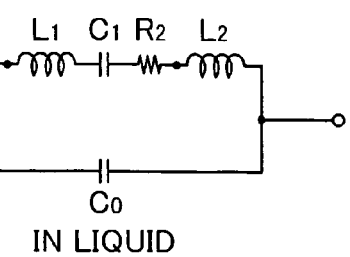
Figure 15:
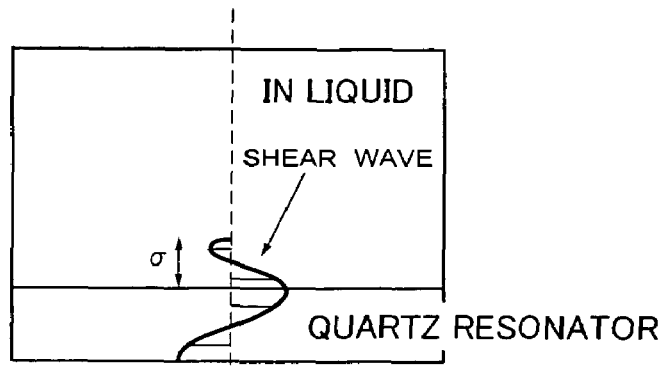
FIG. 15 is a view illustrating attenuation of a shear wave entering a liquid from a quartz resonator.
Figure 16:
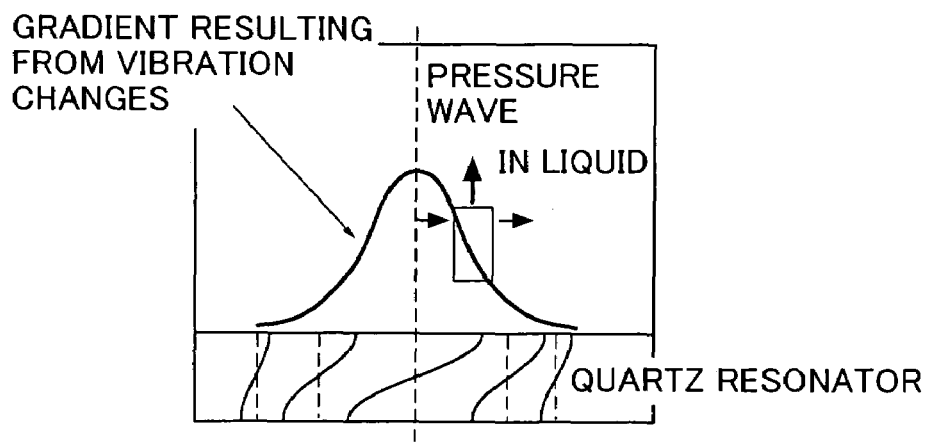
FIG. 16 is a view illustrating a compression wave giving rise to a standing wave.
Figure 18:
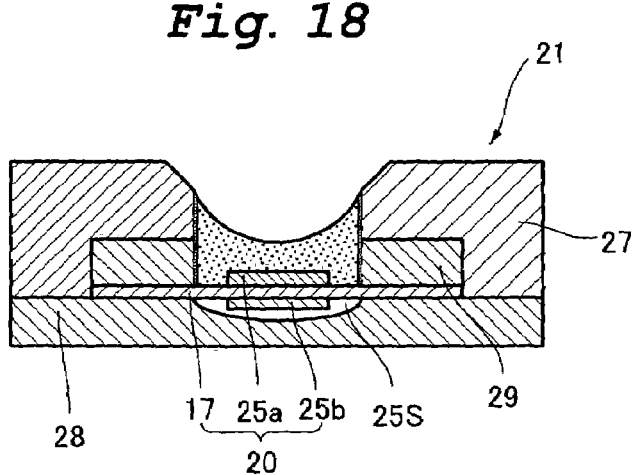
FIG. 18 is a sectional view of a cell of another preferred embodiment of a biosensor apparatus according to the invention.

When performing measurement with respect to very small liquid droplets, it is preferable to use a cell for measuring very small liquid droplets of the kind shown in FIGS. 13A and 13B or FIG. 18.

In the cell 21 shown in FIGS. 13A and 13B, a resonator 20 is made up of a crystal plate 17 and electrodes 18 and 19 provided on opposite sides of the crystal plate 17; concave parts 23a and 23b are provided in a substrate 22 of a few millimeters in thickness, and the resonator 20 is disposed in the concave part 23b.

In the cell 21 shown in FIG. 18, a resonator 20 made up of a crystal plate 17 and electrodes 25a and 25b provided on both sides of the crystal plate 17 is sandwiched between two fixing plates 27, 28 of a few millimeters in thickness along with a seal member 29. A circular hole is provided in the fixing plate 27 above the resonator 20, and a space 25s for accommodating the electrode 25b is formed in the fixing plate 28 below the resonator 20.

Figure 19A:
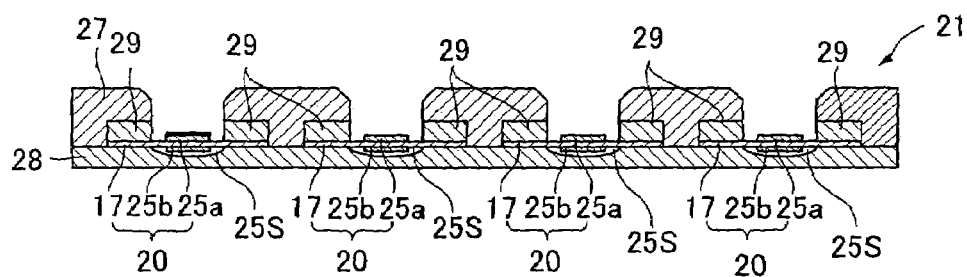
FIG. 19A is a sectional view and FIG. 19B a plan view of cells of another preferred embodiment of a biosensor apparatus according to the invention.
Figure 19B:
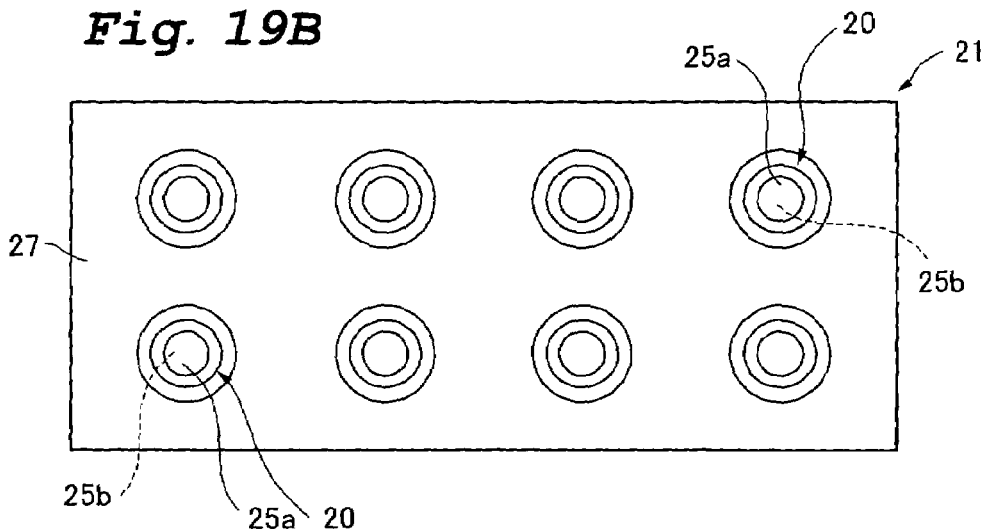

And, preferably, in a cell for very small liquid droplet measurement, multiple cells are disposed on a substrate adjacently. This is because measurement of many samples can then be carried out simultaneously, and furthermore the ease of exchange operations becomes extremely good. The construction for disposing multiple cells adjacently on a substrate is not particularly limited, and may be for example a method wherein multiple resonators are placed on a substrate adjacently. As specific example, as shown in sectional view in FIG. 19A and plan view in FIG. 19B, eight resonators 20 can be disposed adjacently in two rows and four columns and each fixed between fixing plates 27, 28 of a few millimeters in thickness along with a seal member 29. A circular hole is formed in the fixing plate 27 above each resonator 20, and a space 25s for receiving the electrode 25 is formed in the fixing plate 28 below each resonator 20.

And, when the cell for very small liquid droplet measurement described above is used to perform a measurement on an object of measurement such as protein prepared by being mixed with a biochemical buffer liquid including NaCL or KCl or the like, preferably the liquid on the cell is agitated by being discharged and sucked up with a pipette.

Also, preferably the cell is placed in a humidified atmosphere. This is because in this case, even if the sample is very small, because water in the sample does not evaporate readily, accurate measurement becomes possible, and the reaction can be measured accurately over a long period.

Specific examples include the method of placing the cell in a predetermined space and providing a humidifying liquid channel in the vicinity of the cell, the method of providing a cover so as to surround the cell from above and providing an inlet opening in the cover for introducing a humidified gas and feeding humidified gas through the inlet opening, and combinations of these methods.

And, also, when using a very small amount of sample solution for measurement, it is preferable for the sample solution to be brought into contact with the electrode surface only. This is because when oscillation is carried out at a resonant frequency of the resonator and frequency changes are measured, or when an impedance analyzer or a network analyzer is used to measure the frequency of a resonance point (point at which the impedance is a minimum) continuously, the occurrence of frequency change in a fixed direction (drift) can be suppressed, and accurate measurement is possible without correcting this frequency change (drift).

A very small quantity will be taken to mean, when the oscillating frequency of the resonator is made 9 MHz, making the quantity of sample solution placed on the electrode surface not more than the quantity obtained by multiplying the diameter of the electrode (mm) by the coefficient 12.5 μl/mm, or, when the oscillating frequency of the resonator is made 27 MHz, making the quantity of sample solution placed on the electrode surface not more than the quantity obtained by multiplying the diameter of the electrode (mm) by the coefficient 12.0 μl/mm.

And, also, to make it easy to bring the sample solution into contact with the electrode surface only, preferably the crystal plate surface around the electrode is made water-repellent. This water-repellency may be provided by any suitable means, and examples include applying or vapor-depositing a water-repellent substance such as siloxane on the surface of the crystal plate and making the crystal plate with a water-repellent material.

On the face of the side of the electrode of the resonator described above that makes contact with the liquid, a reaction film made of a material that reacts with the specified component or adsorbs the specified component may be provided.

And, although in the foregoing description a network analyzer was used, as long as it can measure the real number part and the imaginary number part of an impedance spectrum there is no particular limitation to this, and it is also possible to use for example an impedance analyzer or the like.

When a network analyzer or an impedance analyzer or the like is used, normally a calibration is carried out before the actual measurement, and preferably a calibration unit formed so as to be interchangeable with the cell having multiple resonators is used.

Figure 20:
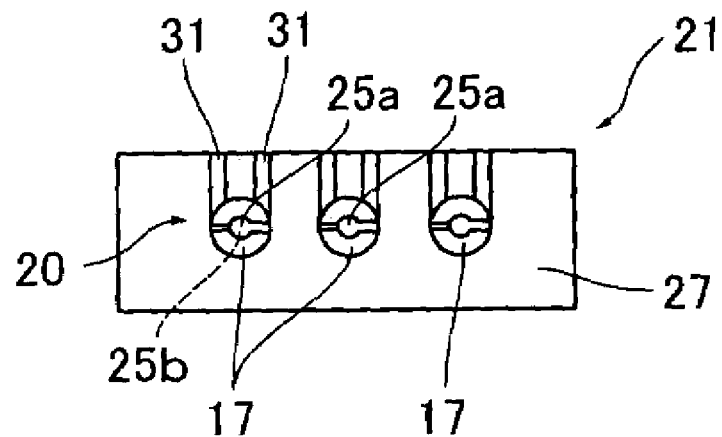
FIG. 20 is a sectional view of cells of another preferred embodiment of a biosensor apparatus according to the invention.
Figure 21:
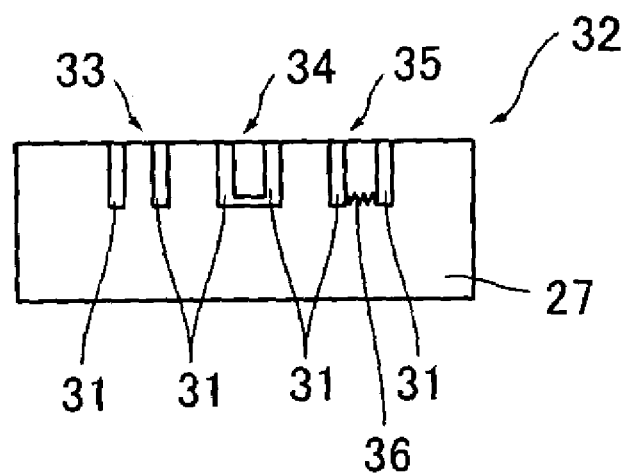
FIG. 21 is a view illustrating a calibration unit for use with a biosensor apparatus according to the invention.

For example, as shown in FIG. 20, when measurement is carried out using a cell 21 made by providing three quartz resonators 20 and providing lead parts 31, 31 for applying a signal to each of the resonators 20, a calibration unit 32 of the kind shown in FIG. 21 is preferably used.

The calibration unit 32 shown in FIG. 21 has calibration electrodes 33, 34, 35 each formed using one pair of lead parts 31, 31. In the example shown in the figure, the calibration electrode 33 is constructed by making the ends of its lead parts 31, 31 open ends so that it becomes an OPEN electrode, the calibration electrode 34 is made by connecting the ends of its lead parts 31, 31 so that it becomes a SHORT electrode, and the calibration electrode 35 is made by providing a predetermined load (resistance) 36 across the ends of its lead parts 31, 31 so that it becomes a LOAD electrode.

This calibration unit is not particularly limited in type as long as it can be connected so that it is interchangeable with the terminals to which the resonators are connected in the measuring system.

The shape of the substrate is preferably the same shape as the substrate used in the cell having the resonators. In this case it becomes unnecessary to prepare a substrate of a new shape for the calibration unit, and its manufacturing cost can be kept down. And, it is possible to use the structure for fixing the device in the measuring system without changing it.

And, as the calibration electrodes, although OPEN electrodes, SHORT electrodes or LOAD electrodes or the like can be provided, it is preferable to provide electrodes of different types. This is because it makes it possible to reduce the number of calibration operations.

Next, specific embodiments of the invention will be described.

Comparison experiments were carried out to compare embodiments of the invention with related art, using the following conditions.

EXPERIMENT EXAMPLE 1

Figure 5:
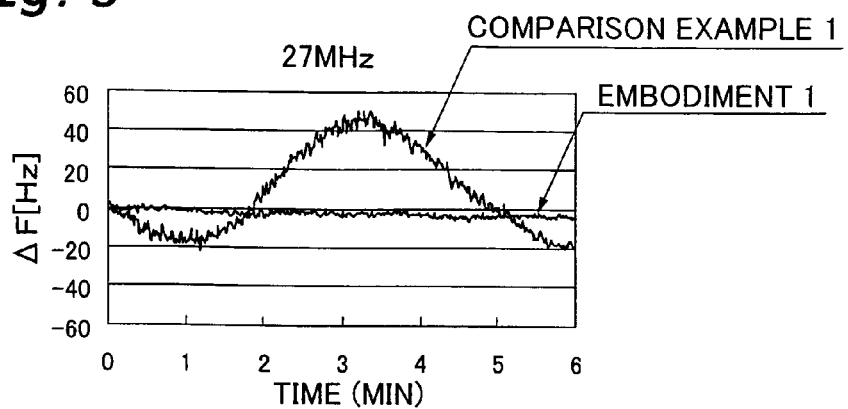
FIG. 5 is a graph showing measurement results of an Embodiment 1 and a Comparison Example 1.

A quartz resonator of fundamental oscillation frequency 27 MHz, diameter 8.9 mm was mounted at the bottom of a substantially cylindrical cell of the kind shown in FIG. 17, and 500 ml of pure water was poured into this cell; a measurement example in which the resonant frequency at the fundamental harmonic was used was taken as Comparison Example 1, a measurement example in which the frequency thrice the resonant frequency at the fundamental harmonic was used was taken as Embodiment 1, and the results are shown in FIG. 5.

From FIG. 5, in Comparison Example 1, a frequency fluctuation (about 70 Hz) arose with a period of about five minutes. With respect to this, in Embodiment 1, the frequency fluctuation (about 5 Hz) was about 6% of that in Comparison Example 1.

The drop in the liquid surface due to evaporation over five minutes of measuring time was 25 mm. This value is about half the wavelength 54 mm of a 27 MHz pressure wave (when the speed of sound at liquid temperature 25° C. is taken as about $1.45 \times 10^3$ m/s), giving the result that this matches the period of the pressure wave. From this result, it was seen that in Comparison Example 1, due to evaporation the liquid surface fell and caused waviness in the frequency.

EXPERIMENT EXAMPLE 2

Figure 6:
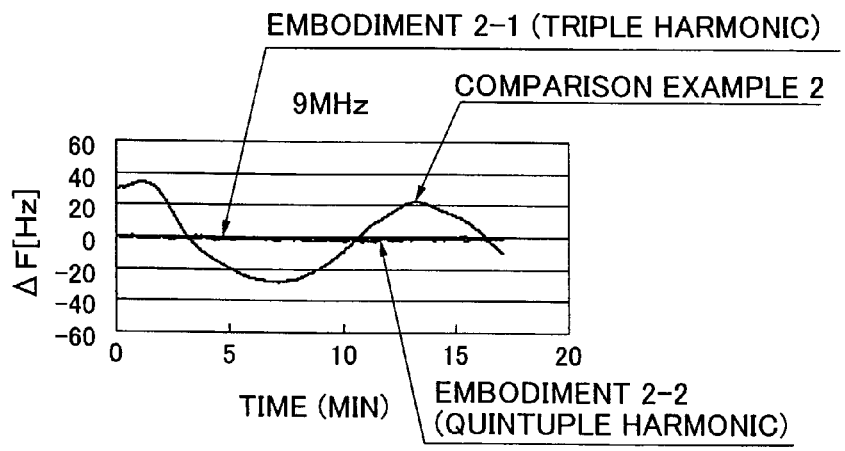
FIG. 6 is a graph showing measurement results of an Embodiment 2-1, an Embodiment 2-2 and a Comparison Example 2.

A quartz resonator of fundamental oscillation frequency 9 MHz, diameter 8.9 mm was mounted at the bottom of a substantially cylindrical cell, and 500 ml of pure water was poured into this cell; a measurement example in which the resonant frequency at the fundamental harmonic was used was taken as Comparison Example 2, measurement examples in which the frequencies thrice and five times the resonant frequency at the fundamental harmonic were used were taken as Embodiments 2-1 and 2-2, and the results are shown in FIG. 6.

From FIG. 6, in Comparison Example 2, a frequency fluctuation (about 48 Hz) arose with a period of about fifteen minutes. With respect to this, the frequency fluctuations in Embodiments 2-1 and 2-2 were about 6% (Embodiment 2-1: about 3 Hz) and 2% (Embodiment 2-2: about 1 Hz) of that in Comparison Example 2.

The drop in the liquid surface due to evaporation over fifteen minutes of measurement time was 75 mm. This value is about half the 159 mm that is the wavelength of the pressure wave arising during oscillation at 9 MHz (when the speed of sound at liquid temperature 25° C. is taken as about $1.45 \times 10^3$ m/s) From this result, it was seen that in Comparison Example 2, due to evaporation the liquid surface fell and caused waviness in the frequency.

EXPERIMENT EXAMPLE 3

Next, an experiment was carried out of bringing a 5 µl droplet of pure water into contact with the electrode of a quartz resonator of fundamental oscillation frequency 27 MHz, diameter 8.9 mm with the environment of the electrode made a humidified atmosphere (air temperature 25° C., humidity at least 90%) to exclude the effect of falling of the liquid surface caused by evaporation.

Figure 7:
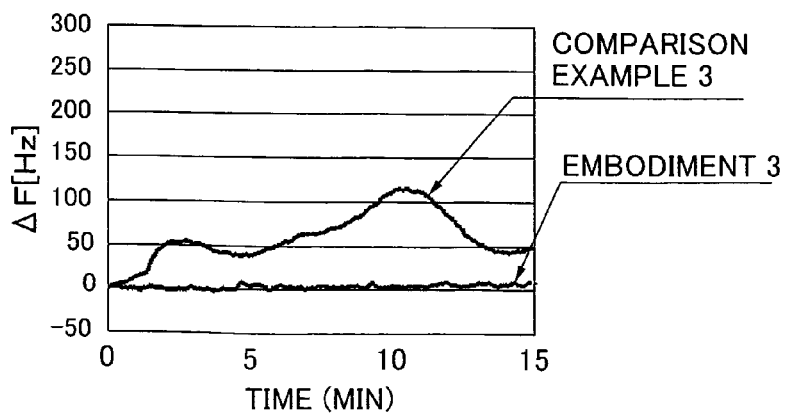
FIG. 7 is a graph showing measurement results of a Comparison Example 3 and an Embodiment 3.

An example in which the resonant frequency at the fundamental harmonic was used was taken as Comparison Example 3 and an example in which the frequency thrice the resonant frequency at the fundamental harmonic was used was taken as Embodiment 3, and the respective results are shown in FIG. 7.

From FIG. 7, whereas in Comparison Example 3 the frequency fluctuated greatly throughout the measurement period, in Embodiment 3 there was almost no frequency fluctuation.

From this result it was seen that in Embodiment 3, frequency fluctuation arising due to causes other than liquid surface drop due to evaporation had also been suppressed.

EXPERIMENT EXAMPLE 4

An experiment was carried out in which a 5 ml droplet of pure water was placed on the electrode of a quartz resonator of fundamental oscillation frequency 27 MHz, diameter 8.9 mm and then after fifteen minutes 1 ml of BlockAce was added.

Figure 8:
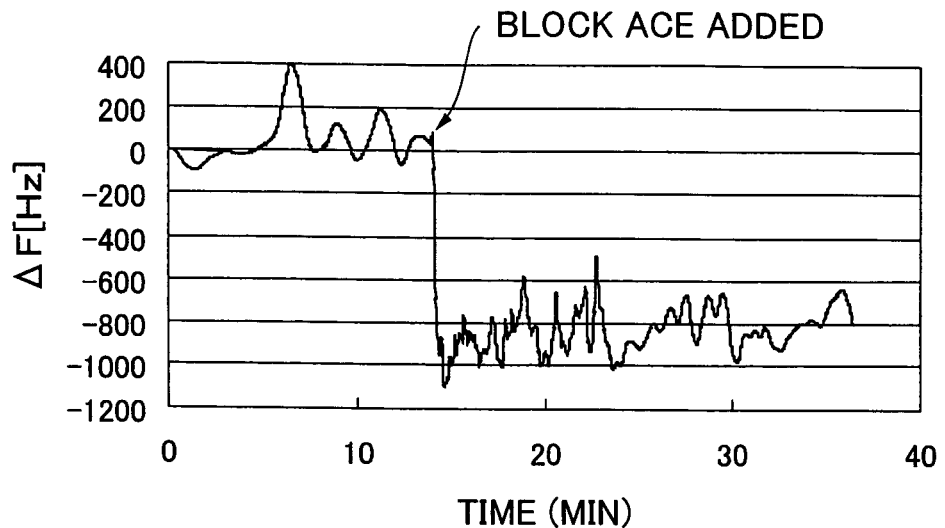
FIG. 8 is a graph showing measurement results of a Comparison Example 4.
Figure 9:
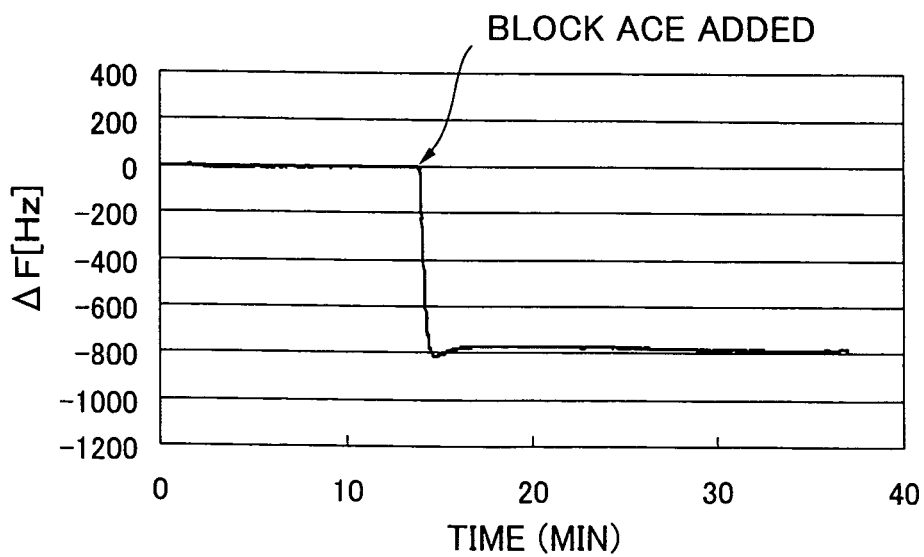
FIG. 9 is a graph showing measurement results of an Embodiment 4.

An example in which the resonant frequency at the fundamental harmonic was used was taken as Comparison Example 4, an example in which the frequency thrice the resonant frequency at the fundamental harmonic was used for the measurement was taken as Embodiment 4, and the respective results are shown in FIG. 8 and FIG. 9.

Whereas in Comparison Example 4 the frequency fluctuated greatly throughout the measurement period, in Embodiment 4 there was almost no frequency fluctuation.

In Embodiment 4, because the frequency thrice the fundamental oscillation frequency was used, the sensitivity was tripled. Because of this, to match the scale to the frequency fluctuation of Comparison Example 4, the frequency fluctuation results of Embodiment 4 were multiplied by ⅓.

In the foregoing Experiment Examples 1 to 4, in Comparison Examples 1 to 4, a frequency fluctuation of 48 Hz in the case of the 9 MHz quartz resonator and 70 Hz in the case of the 27 MHz quartz resonator arose. From the fact that when measuring frequency changes caused by bonding of organic molecules such as DNA and antigen-antibodies it is necessary to measure frequency changes at the 100 to 1000 Hz level, it can be seen that these Comparison Examples 1 to 4 would give large errors. With respect to this, it was found that the frequency fluctuations in Embodiments 1 to 4 were very slight, at around 3 to 5 Hz, and their effects on measurement are very small.

EXPERIMENT EXAMPLE 5

Next, using the same N-tuple harmonic throughout, an experiment was carried out in which Embodiments 5-1 and 5-2 wherein the sample solution was brought into contact with the electrode and parts of the quartz resonator other than the electrode were compared with an Embodiment 5-3 wherein the sample solution was brought into contact with only the electrode of the quartz resonator.

Figure 10:
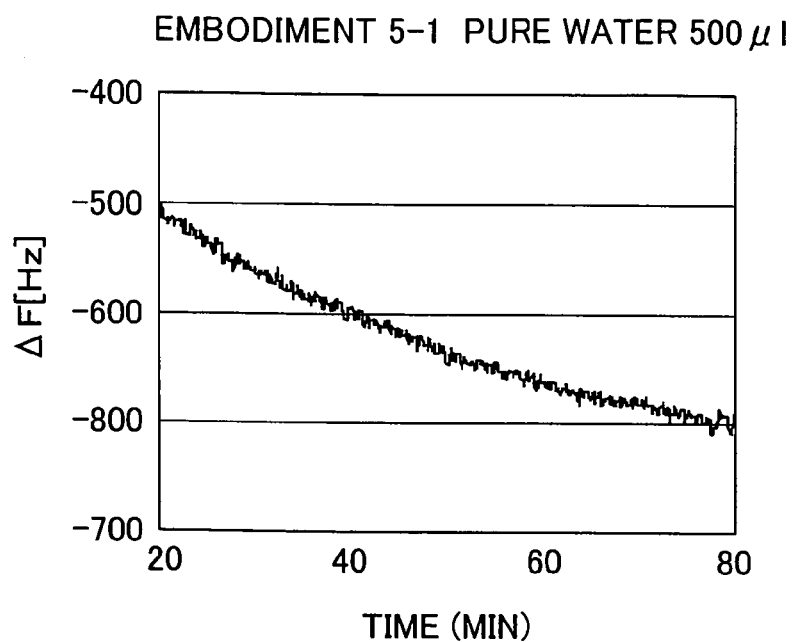
FIG. 10 is a graph showing measurement results of a Comparison Example 5-1.
Figure 11:
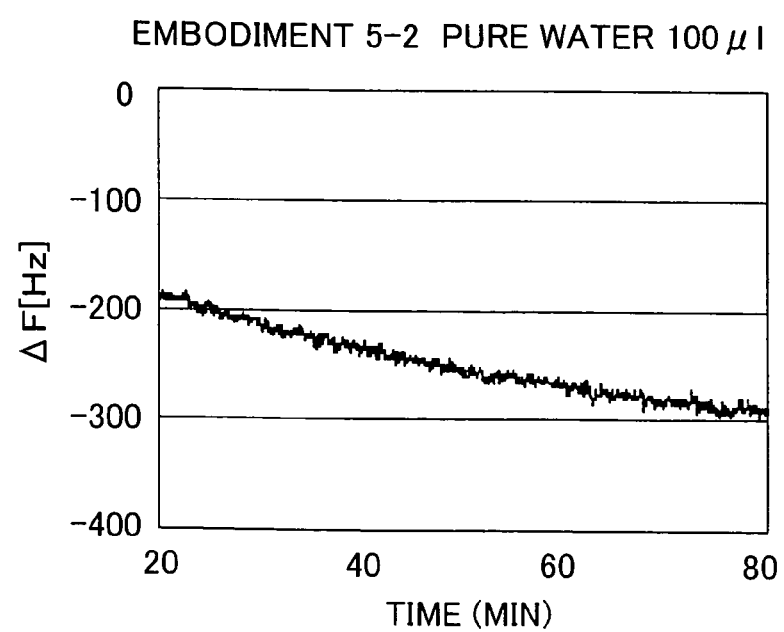
FIG. 11 is a graph showing measurement results of a Comparison Example 5-2.

First, a quartz resonator of fundamental oscillation frequency 27 MHz, diameter 8.9 mm (electrode diameter 2.5 mm) was mounted at the bottom of a substantially cylindrical cell of the kind shown in FIG. 17; a measurement example in which 500 µl of pure water was poured into this cell and the resonant frequency at the triple harmonic was used was taken as Embodiment 5-1, a measurement example in which 100 µl of pure water was poured into a cell of the same shape and the resonant frequency at the triple harmonic was used was taken as Embodiment 5-2, and the respective results are shown in FIG. 10 and FIG. 11.

Then, as Embodiment 5-3, a measurement was carried out using the cell shown in FIGS. 13A and 13B. In the cell 21 shown in FIG. 13A is provided a quartz resonator 20 having a first electrode 18 and a second electrode 19 of diameter 2.5 mm on opposite sides of a quartz plate 17 of fundamental oscillation frequency 27 MHz, diameter 8.9 mm. As shown in FIG. 13B, this quartz resonator 20 is mounted in a concave part 23, the deeper of a concave part 23 and a concave part 24 provided concentrically at two depths from the surface of an acrylic resin plate 22. At the top of the quartz resonator 20, a space for holding the sample solution is formed by the shallower concave part 24 so that a very small amount of sample solution can be easily placed on the first electrode 18 from outside. The surface of the quartz resonator 7 around the electrodes 17, 18 in the cell 21 shown in FIGS. 13A and 13B was made water-repellent by being coated with siloxane.

Figure 12:
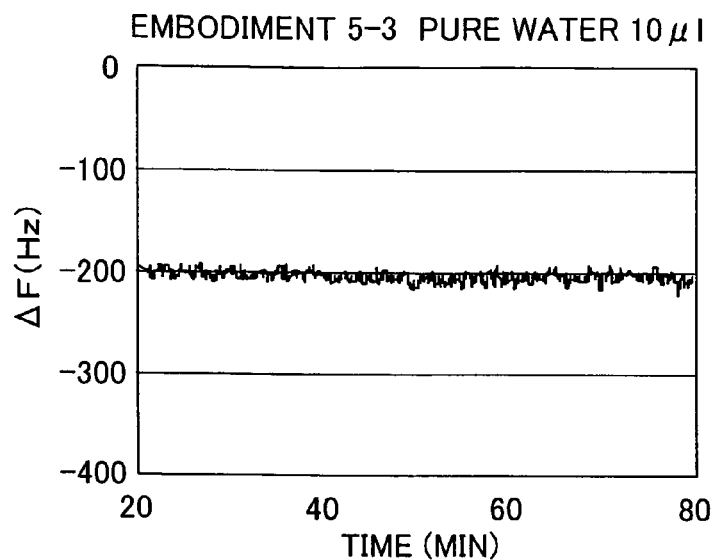
FIG. 12 is a graph showing measurement results of an Embodiment 5-3.

A measurement example in which a 10 µl droplet of pure water was placed on only the first electrode 18 of this cell 21 and the resonant frequency at the triple harmonic was used was taken as Embodiment 5-3, and the results are shown in FIG. 12.

From FIG. 10 to FIG. 12, in Embodiment 5-1, although waviness did not arise within a short time, over sixty minutes a frequency change in a fixed direction (drift) of about −200 Hz (−3.3 Hz per minute) occurred. Similarly in Embodiment 5-2 also, although waviness did not arise within a short time, over sixty minutes a frequency change in a fixed direction (drift) of about −100 Hz (−1.6 Hz per minute) occurred. With respect to this, in Embodiment 5-3, even after sixty minutes the frequency change was approximately 0 Hz.

What is claimed is:

1. A measurement method in which a sample solution is brought into contact with one side of a resonator having first and second electrodes on opposite sides of a crystal plate and an a.c. signal is applied across the first and second electrodes and a frequency change of the resonator is measured from a relationship between the frequency of the a.c. signal and an electrical characteristic of the resonator, wherein the resonator is made to oscillate at an N-tuple harmonic (N=3, 5, 7 . . . ) as the frequency change is measured.

2. A measurement method according to claim 1, wherein the sample solution is brought into contact with the surface of one of the electrodes.

3. A measurement method according to claim 1 or claim 2, wherein the resonator is disposed in a humidified atmosphere.

4. A biosensor apparatus comprising a resonator having first and second electrodes on opposite sides of a crystal plate, wherein a sample solution is brought into contact with one side of the resonator, and wherein an a.c. signal is applied across the first and second electrodes and a frequency change of the resonator is measured from a relationship between the frequency of the a.c. signal and an electrical characteristic of the resonator, wherein the resonator is made to oscillate at an N-tuple harmonic (N=3, 5, 7 . . . ) as the frequency change is measured.

5. A biosensor apparatus according to claim 4, wherein the sample solution is brought into contact with the surface of one of the electrodes.

6. A biosensor apparatus according to claim 4 or claim 5, comprising a cell for holding the sample solution in contact with the resonator, wherein the amount of sample solution held by the cell is less than 100 µl.

7. A biosensor apparatus according to claim 5, wherein when the oscillation frequency of the resonator is made 9 MHz the amount of sample solution brought into contact with the electrode surface is not greater than the amount obtained by multiplying the diameter of the electrode (mm) by the coefficient 12.5 µl/mm.

8. A biosensor apparatus according to claim 5, wherein when the oscillation frequency of the resonator is made 27 MHz the amount of sample solution placed on the electrode surface is not greater than the amount obtained by multiplying the diameter of the electrode (mm) by the coefficient 12.0 µl/mm.

9. A biosensor apparatus according to claim 4 or claim 5, wherein the surface of the crystal plate around the electrode is water-repellent.

10. A biosensor apparatus according to claim 4 or claim 5, comprising a plurality of resonators disposed adjacently on a substrate.

* * * * *